United States Patent [19]
Shi et al.

[11] Patent Number: 6,136,962
[45] Date of Patent: Oct. 24, 2000

[54] COVALENT ATTACHMENT OF UNMODIFIED NUCLEIC ACIDS TO SILANIZED SOLID PHASE SURFACES

[75] Inventors: Jufang Shi, Baltimore; Michael T. Boyce-Jacino, Finksburg, both of Md.

[73] Assignee: Orchid BioSciences, Inc., Princeton, N.J.

[21] Appl. No.: 09/102,371

[22] Filed: Jun. 23, 1998

Related U.S. Application Data

[63] Continuation of application No. 08/870,010, Jun. 6, 1997, Pat. No. 5,919,626.

[51] Int. Cl.[7] .................................................. C07H 21/04
[52] U.S. Cl. .................... 536/23.1; 536/24.3; 536/24.31; 536/24.32; 536/24.33
[58] Field of Search ................................ 536/23.1, 24.3, 536/24.31, 24.32, 24.33; 422/104

[56] References Cited

U.S. PATENT DOCUMENTS

| | | | |
|---|---|---|---|
| 4,521,509 | 6/1985 | Benkovic et al. | 435/6 |
| 4,656,127 | 4/1987 | Mundy | 435/6 |
| 5,075,217 | 12/1991 | Weber | 435/6 |
| 5,175,082 | 12/1992 | Jeffreys | 435/6 |
| 5,302,509 | 4/1994 | Cheeseman | 435/6 |
| 5,518,900 | 5/1996 | Nikiforov et al. | 435/91.1 |

FOREIGN PATENT DOCUMENTS

| | | |
|---|---|---|
| 2650840 | 8/1989 | France . |
| WO 90/11369 | 10/1990 | WIPO . |
| WO 90/13668 | 11/1990 | WIPO . |
| WO 91/14003 | 9/1991 | WIPO . |
| WO 92/15712 | 9/1992 | WIPO . |
| WO 95/17676 | 6/1995 | WIPO . |

OTHER PUBLICATIONS

Pål Nyrén, et al., Solid Phase DNA Minisequencing by an Enzymatic Luminometric Inorganic Pyrophosate Detection Assay, (1993), Analytical Biochemistry 208, 171–175.

Ann–Christine Syvänen, et al. Identification of Individuals by Analysis of Biallelic DNA Markers, Using PCR and Solid–Phase Minisequencing, (1993) Am. J. Hum. Genet. 52:46–59.

Mohan N. Kuppuswamy, et al., Single nucleotide primer extension to detect genetic diseases: Experiental application to hemophilia B (factor IX) and cystic fibrosis genes, (Feb. 1991), Proc. Natl. Acad. Sci. USA vol. 88, pp. 1143–1147.

Deborah A. Nickerson, et al., Automated DNA diagnostics using an ELISA–based oligonucleotide ligation assay, (Nov. 1990) Proc. Natl. Acad. Sci. USA vol. 87, pp. 8923–8927.

Ulf Landegren, A. Ligase–Mediated Gene Detection Technique, (Aug. 26, 1988), Sci. vol. 241, pp. 1077–1080.

Arthur Kornberg, et al., Deoxyribonucleases, DNA Replication. Second Edition (1992).

J. Hillel, et al. DNA Fingerprints Applied to Gene Introgression in Breeding Programs (Mar. 1990), Genetics 124: 783–789.

J. Hillel, et al., DNA fingerprints of poultry, (1989), Animan Genetics, 20. 145–155.

Russell G. Higuchi, et al., Production of single–stranded DNA templates by exonuclease digestion following the polymerase chain reaction, (Nov. 14, 1989, vol. 17.

Ulf B. Gyllensten, et al., Generation of single–stranded DNA by the polymerase chain reaction and its application to direct sequencing of the HLA–DQA locus, (Oct. 1988) Proc. Natl. Acad. Sci. USA vol. 85, pp. 7652–7656.

Mirta Mihovilovic, et al., Biotechniques, (1989) vol. 7, No. 1.

Uwe Maskos, et al., Oligonucleotide hybridisations on glass supports: a novel linker for oligonucleotidynthesis and hybridisation properties of oligonucleotides synthesised in situ, (1992) Nucleic Acids Research, vol. 20, No. 7 1679–1684.

Ann–Christine Syvänen, A Primer–Guided Nucleotide Incorporation Assay in the Genotyping of Apolipoprotein E, (1990) Genomics 8, 684–692.

Søren Richard Rasmussen, et al., Covalent Immobilization of DNA onto Polystyrene Microwells: The Molecules Are only Bound at the 5' End (1991) Analytical Biochemistry 198, 138–142.

Mark X. Sliwkowski, et al., Resolution of sulphydryl oxidase from γ–glutamyltransferase in bovine milk by alent chromatogaphy on cysteinylsuccinamidoproply–glass, (1991) Biochem. J. 209, 731–739. vol. 209.

Eoin Fahy, et al., Design and synthesis of polyacrylamide–based oligonucleotide supports for use in nucleic acid diagnostics, (1993) Nucleic Acids Research, vol. 21, No. 8 1819–1826.

A.J. Jeffreys, et al., DNA fingerprints of dogs and cats (1987) Animal Genetics, 18, 1–15.

L. Jones, Identical twin marrow transplantation for 5 patients with chronic myeloid leukaemia: Role of DNA finger–printing to confirm monozygosity in 3 cases, (1987) Eur J Haematol 39:144–147.

S. S. Moore, et al., The Conservation of Dinucleotide Microsatellites among Mammalian Genomes Allow Use of Heterologous PCR Primer Pairs in Closely Related Species (1991) Genomics 10, 654–660–.

Ian C. Gray, et al., Evolutionary transience of hypervariable minisatellites in man and the primates (1991) Proc. R. Soc. Lond. B. 243, 241–253.

A. J. Jeffreys, et al., Individual–specific 'fingerprints' of human DNA (Jul. 4, 1985) Nature vol. 316.

Alec J. Jeffreys, et al., DNA "Fingerprints" and Segregation Analysis of Multiple Markers in Human Pedigrees (1986) *Am J Hum Genet* 39:11–24.

(List continued on next page.)

*Primary Examiner*—Kenneth R. Horlick
*Attorney, Agent, or Firm*—Kalow & Springut LLP

[57] ABSTRACT

This invention relates to a composition having a nucleic acid molecule covalently coupled to a solid support by means of a covalent linkage. The nucleic acid molecule is covalently coupled to the solid support by a silane. The composition can be used in nucleic acid hybridization assays and sequencing by hybridization assays.

16 Claims, 2 Drawing Sheets

OTHER PUBLICATIONS

Theo T. Nikiforov, et al., The Use of Phosphorothioate Primers and Exonuclease Hydrolysis for the Preparation of Single–stranded PCR Products and their Detection by Solid– phase Hybridization (1994) 3:285–291.

M.H. Skolnick and et al., Strategies for detecting and characterizing restriction fragment length polymorphisms (RFLP's) (1982) Cytogenet. Cell Genet. 32: 58–67.

John A.L. Armour, et al., Recent advances in minisatellite biology, (Jul. 1992) vol. 307, No. 1, 113–115.

J. F. Gusella, DNA Polymorphism and Human, (1986) Ann. Rev. Bichem. 55:831–54.

Theo T. Nikiforov, et al., Genetic Bit Analysis: a solid phase method for typing single nucleotide polymorphisms (1994) Nucleic Acids Research, vol. 22, No. 20 4167–4175.

Patrik Dahlén, et al., Sensitive detection of genes by sandwich hybridization and time–resolved fluorometry, (1987) Molecular and Cellular Probes 1. 159–168.

N.D. Sinha, et al., Polymer support oligonucleotide synthesis XVIII: use of β–cyanoethyl–N–dialkylamino–/N–morpholino phosphoramidite of deoxynucleosides for the synthesis of DNA fragments simplifying deprotection and isolation of the final product (1984) vol. 12 No. 11.

E.M. Southern, et al. Arrays of complementary oligonucleotides for analysing the hybridisation behaviour of nucleic acids (1994) Nucleic Acids Research, vol. 22, No. 8, 1368–1373.

Ann Caviani Pease, et al., Light–generated oligonucleotide arrays for rapid DNA sequence analysis, (May 1994) Proc. Natl. Acad. Sci. USA vol. 91, pp. 5022–5026.

Zhen Guo, et al., Direct fluorescence analysis of genetic polymorphisms by hybridization with oligonucleotide arrays on glass supports (1994) Nucleic Acids Research, vol. 22, No. 24 pp. 5456–5465.

Johann Ott, et al., Protection of Oligonucleotide Primers against Degradation by DNA Polymerase I, (1987) Bochemistry, 26, 8237–8241.

Fritz Eckstein, et al. Synthesis and Properties of Diastereoisomers of Adenosine 5'–(O–1–Thiotriphosphate) and Adenosine 5'–(O–2–Thiotriphosphate), (1976) Biochemistry, vol. 15, No. 8.

K.R. Khrapko, et al., A method of DNA sequencing by hybridization with oligonucleotide matrix, (1992) DNA Sequence vol. 1, pp. 375–388.

Stanley Tabor, et al., Effect of manganese ions on the incorporation of dideoxynucleotides by bacteriophage T7 DNA polymerase and *Escherichia coli* DNA polymerase I, (Jun. 1989) Proc. Natl. Acd. Sci. USA vol. 86, pp. 4076–4080.

Luis Ugozzoli, et al., Detection of Specific Alleles by Using Allele–Specific Primer Extension Followed by Capture on Solid Support (1991) GATA 9(4): 107–112.

Jon R. Sayers, 5'—3' Exonucleases in phosphorothiate–based oligonucleotide–directed mutagenesis, (1988) vol. 16, No. 3.

David Botstein, et al., Construction of a Genetic Linkage Map in Man Using Restriction Fragment Length Polymorphisms, (1980)) Genet 32:314–331/.

Mickey S. Urdea, A novel method for the rapid detection of specific nucleotide sequences in crude biogical samples without blotting or radioactivity; application to the analysis of hepatitis B virus in human serum, (1987) Gene, 61, pp. 253–264.

Kim Holmstrøm, A highly Sensitive and Fast Nonradioactive Method for Detection of Polymerase Chain Reaction Products, Analytical Biochemistry 209, 278–283 (1993).

Marjut Ranki, et al., Sandwich hybridization as a convenient method for the detection of nucleic acids in crude, Gene, 21 (1983) 77–85.

George H. Keller, Detection of Hjuman Immunodeficiency Virus Type 1 DNA by Polymerase Chain Reaction Amplification and Capture Hybridization in Microtiter Wells, (Mar. 1991) Journal of Clinical Microbiology, pp. 638–641.

Kenneth L. Beattle, et al., Advances in Genosensor Research (1995) Clin. Chem. 41/5. 700–706.

Jagannath B. Lamture, et al., Direct detection of nucleic acid hybridization on the surface of a charge coupled device (1994) Nucleic Acids Research vol. 22, No. 11 2121–21.

Don I. Stimpson, et al., Real–time detection of DNA hybridization and melting on oligonucleotide arrays using optical wave guides (Jul. 1995) Proc. Natl. Acad. Sci. USA vol. 92, pp. 6379–6383.

Linda A. Chrisey, et al. Covalent attachment of synthetic DNA to self–assembled monolayer films (1996) Nucleic Acids Research, vol. 24, No. 15 3031–3039.

COVALENT ATTACHMENT OF UNMODIFIED NUCLEIC ACIDS TO SILANIZED SOLID PHASE SURFACES

CROSS-REFERENCE TO RELATED APPLICATIONS

This application is a continuation of U.S. patent application Ser. No. 08/870,010 (filed Jun. 6, 1997), U.S. Pat. No. 5,919,626.

FIELD OF THE INVENTION

The invention relates to a simple, and preferably cost effective, method for immobilizing nucleic acid molecules onto a solid support. The invention further concerns the use of such immobilized molecules in nucleic acid hybridization assays, sequencing by hybridization assays, and genetic analyses and combinatorial analyses involving nucleic acids or proteins for screening applications.

BACKGROUND OF THE INVENTION

The analysis of the structure, organization and sequence of nucleic acid molecules is of profound importance in the prediction, diagnosis and treatment of human and animal disease, in forensics, in epidemiology and public health, and in the elucidation of the factors that control gene expression and development. Methods for immobilizing nucleic acids are often important in these types of analyses. Three areas of particular importance involve hybridization assays, nucleic acid sequencing, and the analysis of genomic polymorphisms.

I. Nucleic Acid Hybridization

The capacity of a nucleic acid "probe" molecule to hybridize (i.e. base pair) to a complementary nucleic acid "target" molecule forms the cornerstone for a wide array of diagnostic and therapeutic procedures.

Hybridization assays are extensively used in molecular biology and medicine. Methods of performing such hybridization reactions are disclosed by, for example, Sambrook, J. et al. (In: *Molecular Cloning: A Laboratory Manual*, Cold Spring Harbor Laboratory Press, Cold Spring Harbor, N.Y. (1989)), Haymes, B. D., et al. (In: *Nucleic Acid Hybridization, A Practical Approach*, IRL Press, Washington, D.C. (1985)) and Keller, G. H. and Manak, M. M. (In: *DNA Probes, Second Edition*, Stockton Press, New York, N.Y. (1993)) which references are incorporated herein by reference.

Many hybridization assays require the immobilization of one component. Nagata et al. described a method for quantifying DNA which involved binding unknown amounts of cloned DNA to microtiter wells in the presence of 0.1 M $MgCl_2$ (Nagata et al., *FEBS Letters* 183: 379–382, 1985). A complementary biotinylated probe was then hybridized to the DNA in each well and the bound probe measured colorimetrically. Dahlen, P. et al. have discussed sandwich hybridization in microtiter wells using cloned capture DNA adsorbed to the wells (Dahlen, P. et al., *Mol. Cell. Probes* 1: 159–168, 1987). An assay for the detection of HIV-1 DNA using PCR amplification and capture hybridization in microtiter wells has also been discussed (Keller, G. H. et al., *J. Clin. Microbiol.* 29: 638–641, 1991). The NaCl-mediated binding of oligomers to polystyrene wells has been discussed by Cros et al. (French patent no. 2,663,040) and very recently by Nikiforov et al. (*PCR Methods Applic.* 3: 285–291, 1994). The cationic detergent-mediated binding of oligomers to polystyrene wells has very recently been described by Nikiforov et al., *Nucleic Acids Res.* 22: 4167–4175.

II. Analysis Of Single Nucleotide DNA Polymorphisms

Many genetic diseases and traits (i.e. hemophilia, sickle-cell anemia, cystic fibrosis, etc.) reflect the consequences of mutations that have arisen in the genomes of some members of a species through mutation or evolution (Gusella, J. F., *Ann. Rev. Biochem.* 55:831–854 (1986)). In some cases, such polymorphisms are linked to a genetic locus responsible for the disease or trait; in other cases, the polymorphisms are the determinative characteristic of the condition.

Such single nucleotide polymorphisms differ significantly from the variable nucleotide type polymorphisms ("VNTRs"), that arise from spontaneous tandem duplications of di- or tri-nucleotide repeated motifs of nucleotides (Weber, J. L., U.S. Pat. No. 5,075,217; Armour, J. A. L. et al. *FEBS Lett.* 307:113–115 (1992); Jones, L. et. al., *Eur. J. Haematol.* 39:144–147 (1987); Horn, G. T. et al., PCT Application WO91/14003; Jeffreys, A. J., U.S. Pat. No. 5,175,082); Jeffreys. A. J. et al., *Amer. J. Hum. Genet.* 39:11–24 (1986); Jeffreys. A. J. et al., *Nature* 316:76–79 (1985); Gray, I. C. et al., *Proc. R. Acad. Soc. Lond.* 243:241–253 (1991); Moore, S. S. et al., *Genomics* 10:654–660 (1991); Jeffreys, A. J. et al., *Anim. Genet.* 18:1–15 (1987); Hillel, J. et al., *Anim. Genet.* 20:145–155 (1989); Hillel, J. et al., *Genet.* 124:783–789 (1990)), and from the restriction fragment length polymorphisms ("RFLPs") that comprise variations which alter the lengths of the fragments that are generated by restriction endonuclease cleavage (Glassberg, J., UK patent application 2135774; Skolnick, M. H. et al., *Cytogen. Cell Genet.* 32:58–67 (1982); Botstein, D. et al., *Ann. J. Hum. Genet.* 32:314–331 (1980); Fischer, S. G et al. (PCT Application WO90/13668); Uhlen, M., PCT Application WO90/11369)).

Because single nucleotide polymorphisms constitute sites of variation flanked by regions of invariant sequence, their analysis requires no more than the determination of the identity of the single nucleotide present at the site of variation; it is unnecessary to determine a complete gene sequence for each patient. Several methods have been developed to facilitate the analysis of such single nucleotide polymorphisms.

Mundy, C. R. (U.S. Pat. No. 4,656,127), for example, discusses a method for determining the identity of the nucleotide present at a particular polymorphic site that employs a specialized exonuclease-resistant nucleotide derivative. A primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. The Mundy method has the advantage that it does not require the determination of large amounts of extraneous sequence data. It has the disadvantages of destroying the amplified target sequences, and unmodified primer and of being extremely sensitive to the rate of polymerase incorporation of the specific exonuclease-resistant nucleotide being used.

Cohen, D. et al. (French Patent 2,650,840; PCT Appln. No. WO91/02087) discuss a solution-based method for determining the identity of the nucleotide of a polymorphic site. As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis™ or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase. It is thus easier to perform, and more accurate than the method discussed by Cohen.

Cheesman, P. (U.S. Pat. No. 5,302,509) describes a method for sequencing a single stranded DNA molecule using fluorescently labeled 3'-blocked nucleotide triphosphates. An apparatus for the separation, concentration and detection of a DNA molecule in a liquid sample has been recently described by Ritterband, et al. (PCT Patent Application No. WO95/17676).

An alternative approach, the "Oligonucleotide Ligation Assay" ("OLA") (Landegren, U. et al., *Science* 241:1077–1080 (1988)) has also been described as capable of detecting single nucleotide polymorphisms. The OLA protocol uses two oligonucleotides which are designed to be capable of hybridizing to abutting sequences of a single strand of a target. One of the oligonucleotides is biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., *Proc. Natl. Acad. Sci. (U.S.A.)* 87:8923–8927 (1990). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Recently, several primer-guided nucleotide incorporation procedures for assaying polymorphic sites in DNA have been described (Komher, J. S. et al., *Nucl. Acids. Res.* 17:7779–7784 (1989); Sokolov, B. P., *Nucl. Acids Res.* 18:3671 (1990); Syvänen, A.-C., et al., *Genomics* 8:684–692 (1990); Kuppuswamy, M. N. et al., *Proc. Natl. Acad. Sci. (U.S.A.)* 88:1143–1147 (1991); Prezant, T. R. et al., *Hum. Mutat.* 1:159–164 (1992); Ugozzoli, L. et al., *GATA* 9:107–112 (1992); Nyrén, P. et al., *Anal. Biochem.* 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvänen, A.-C., et al., *Amer. J. Hum. Genet.* 52:46–59 (1993)). Such a range of locus-specific signals could be more complex to interpret, especially for heterozygotes, compared to the simple, ternary (2:0, 1:1, or 0:2) class of signals produced by the GBA™ method. In addition, for some loci, incorporation of an incorrect deoxynucleotide can occur even in the presence of the correct dideoxynucleotide (Komher, J. S. et al., *Nucl. Acids. Res.* 17:7779–7784 (1989)). Such deoxynucleotide misincorporation events may be due to the Km of the DNA polymerase for the mispaired deoxy-substrate being comparable, in some sequence contexts, to the relatively poor Km of even a correctly base paired dideoxy-substrate (Kornberg, A., et al., In: DNA Replication, Second Edition (1992), W. H. Freeman and Company, New York; Tabor, S. et al., *Proc. Natl. Acad. Sci. (U.S.A.)* 86:4076–4080 (1989)). This effect would contribute to the background noise in the polymorphic site interrogation.

III. Methods of Immobilizing Nucleic Acids to a Solid Phase

Several of the above-described methods involve procedures in which one or more of the nucleic acid reactants are immobilized to a solid support. Currently, 96-well polystyrene plates are widely used in solid-phase immunoassays, and several PCR product detection methods that use plates as a solid support have been described. The most specific of these methods require the immobilization of a suitable oligonucleotide probe into the microtiter wells followed by the capture of the PCR product by hybridization and colorimetric detection of a suitable hapten. It would be desirable to have an improved immobilization method that could be used to bind oligonucleotides to polystyrene such that their capacity to be used for hybridization, sequencing, or polymorphic analysis would be retained, and which would be rapid, convenient to use and inexpensive. The present invention provides such an improved method.

The means by which macromolecules bind non-covalently to polystyrene and glass surfaces is not well understood. Nevertheless, these adsorption phenomena have proven to be important in the development and manufacturing of immunoassays and other types of diagnostic tests where one component needs to be immobilized.

Polystyrene is a very hydrophobic material because it normally contains no hydrophilic groups. Microtiter plate manufacturers have developed methods of introducing such groups (hydroxyl, carboxylate and others) onto the surface of microwells to increase the hydrophilic nature of the surface. Theoretically, this allows macromolecules to bind through a combination of hydrophobic and hydrophilic interactions (Baier et al., *Science* 162: 1360–1368 (1968); Baier et al., *J. Biomed. Mater. Res.* 18: 335–355 (1984); Good et al., in L. H. Lee (ed.) *Fundamentals of Adhesion*, Plenum, New York, chapter 4 (1989)) (FIG. 1). In practice, some proteins do bind more efficiently to the treated hydrophilic polystyrene than to the untreated material. Covalent binding to polystyrene, especially microtiter wells, has however proven to be difficult, so passive adsorption remains the most commonly used method of binding macromolecules to such wells. The term "polystyrene" may also be used to describe styrene-containing copolymers such as: styrene/divinyl benzene, styrene/butadiene, styrene/vinyl benzyl chloride and others.

While polystyrene is an organic hydrophobic substrate, glass provides an inorganic hydrophilic surface. The most common glass format in immunoassays is the microscope slide. Laboratory-grade glasses are predominantly composed of $SiO_2$, but they also may contain $B_2O_3$, $Al_2O_3$ as well as other oxides (FIG. 2). Interfaces involving such materials have thus become a dynamic area of chemistry in which surfaces have been modified in order to generate desired heterogeneous environments or to incorporate the bulk properties of different phases into a uniform composite structure. Our purpose here then is to use organosilanes for tailoring surfaces with chemically reactive groups mercapto (SH) and/or epoxy.

While numerous methods for the attachment of oligonucleotides and proteins on surfaces have been described, the methods are both expensive and time consuming. The reported covalent attachments of pre-made oligonucleotides onto modified glass surfaces have been always using modified oligonucleotides in order to increase reactivity and selectivity of oligonucleotides towards surfaces. Typical modifications involved the introduction of amino groups, or thio groups into 3'- and/or 5'-oligonucleotides. For example, Stimpson et al. (*P.N.A.S.* 92:6379–6383 (1995)) reported covalent attachment of 3'-amino oligonucleotides onto epoxy silanized surfaces with acid catalysis but with only $\frac{1}{10}$ the density achieved in this invention. Beattie et al. (*Clin. Chem.* 41:700–706 (1995)) reported attachment of 3'- and/or 5'-amino oligonucleotides onto epoxy silanized surfaces under elevated temperature. Lamture et al. (*Nucleic Acids Res.* 22:2121–2125 (1994)) reported the methods for attaching 3'-amino-oligonucleotides onto epoxy silanized slides under 0.1 M KOH. Hetero bifunctional cross-linkages have been used to couple the 3' or 5'-thio-modified oligonucleotides or amino-modified onto amino-propyl silanized surfaces as reported by Chrisey et al. (*Nucleic Acids Res.* 24: 303103039 (1996)) and Guo et al. (*Nucleic Acids Res.* 22: 4556–5465 (1994)). All of these reported methods however, require modified oligonucleotides.

The present invention describes a novel method for immobilizing nucleic acid molecules to a solid-phase by means of a covalent ether or thioether linkage. This simple, two-step method has the specificity and efficiency needed to prepare DNA arrays.

SUMMARY OF THE INVENTION

The present invention provides an improved immobilization method that permits the rapid, and inexpensive immobilization of nucleic acid molecules to a solid phase. The invention allows immobilization of oligonucleotides by incubation with a silane-containing or silane-treated solid phase. The immobilized molecules can be used for nucleic acid hybridization assays, sequencing hybridization assays, genetic analyses, combinatorial analyses involving nucleic acids or proteins, and other screening applications such as protein-DNA binding assays.

In detail, the invention provides a method for immobilizing a nucleic acid molecule to a solid phase, the method comprising the steps of:

(A) coating said solid phase with a silane and allowing said silane-coated solid phase to cure; and (B) coupling unmodified nucleic acid molecules having either a terminal 3' OH or a terminal 5' OH to said silane-coated solid phase.

The invention particularly concerns the embodiments of the above method wherein, in step A, the silane is selected from the group consisting of 3-mercapto-propyl-trimethoxysilane and 3-glycidoxy propyl-trimethoxysilane.

The invention further pertains to oligonucleotide coated surfaces useful in genetic analysis and other screening applications such as protein-DNA binding assays.

The invention particularly concerns oligonucleotide arrays comprising epoxy- or mercapto-silane coated surfaces and unmodified oligonucleotides covalently attached to the epoxy or mercapto-silane, such arrays being useful for nucleic acid hybridization assays, sequencing hybridization assays, genetic analyses, combinatorial analyses involving nucleic acids or proteins, and other screening applications such as protein-DNA binding assays. The features of the coated surface enable standardized patterning of unique oligonucleotides onto silane surface coatings.

The invention further pertains to simultaneous patterning of multiple DNA probes in a high density and in a variety of array formats.

DETAILED DESCRIPTION OF THE INVENTION

Figure 1:
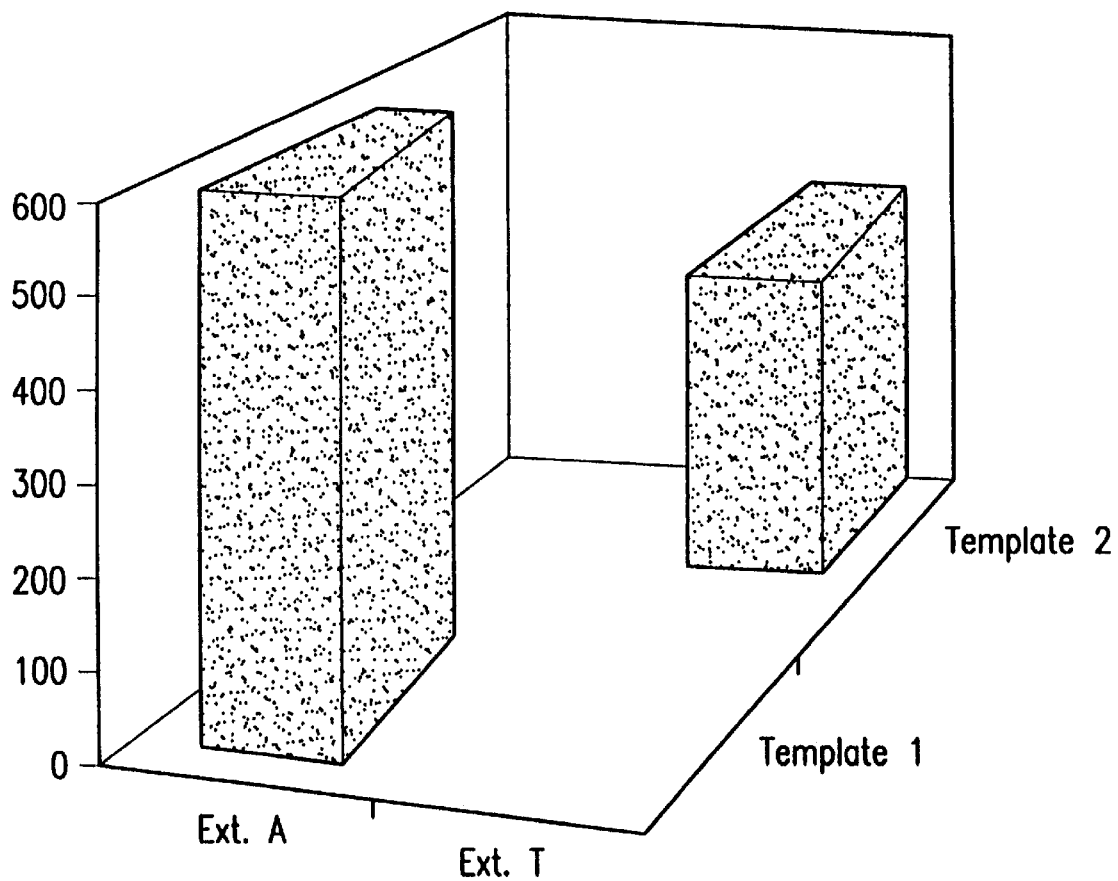
FIG. 1 shows the results of a GBA functional assay of epoxy-based attachment chemistry.

I. The Immobilization of Nucleic Acid Molecules

The present invention concerns a method for immobilizing nucleic acid molecules onto a solid-phase. Recently, several methods have been proposed as suitable for immobilizing an oligonucleotide to a solid support. Holmstrom, K. et al., for example, exploit the affinity of biotin for avidin and streptavidin, and immobilize biotinylated nucleic acid molecules to avidin/streptavidin coated supports (Holmstrom, K. et al.,*Anal. Biochem.* 209:278–283 (1993)). Another method requires the precoating of the polystyrene or glass solid phases with poly-L-Lys or poly L-Lys, Phe, followed by the covalent attachment of either amino- or sulfhydryl-modified oligonucleotides using bi-functional crosslinking reagents. Unlike the present invention, both methods require the use of modified oligonucleotides as well as a pretreatment of the solid phase; however, the present invention discloses a method to covalently bond oligonucleotides with an "unmodified" 5' or 3'-OH to a solid surface. As used herein, the term "unmodified" refers to the absence of any requirement for specialized reactive groups. It does not refer to the exclusion of nucleotides or oligonucleotides that have such groups, or that are biotinylated, flouresceinated, etc.

Kawai, S. et al. describes an alternative method in which short oligonucleotide probes were ligated together to form multimers and these were ligated into a phagemid vector (Kawai, S. et al., *Anal. Biochem.* 209:63–69 (1993)). The oligonucleotides were immobilized onto polystyrene plates and fixed by UV irradiation at 254 nm. A method for the direct covalent attachment of short, 5'-phosphorylated primers to chemically modified polystyrene plates ("Covalink" plates, Nunc) has also been proposed by Rasmussen, S. R. et al., (*Anal. Biochem.* 198:138–142 (1991)). The covalent bond between the modified oligonucleotide and the solid phase surface is created by a condensation reaction with a water-soluble carbodimide. The Rasmussen method claims a predominantly 5'-attachment of the oligonucleotides via their 5'-phosphates; however, it requires the use of specially prepared, expensive plates. The method of the present invention departs from such methods, in not requiring such unstable and difficult to manipulate crosslinking reagents.

Maskos, U. et al. describes a method to synthesize oligonucleotides directly onto a glass support (Maskos, U. et al., *Nucl. Acids Res.* 20:1679–1684 (1992)). According to this method, a flexible linker with a primary hydroxyl group is bound to the solid support via a glycidoxypropyl silane, wherein the primary hydroxyl group serves as the starting point for the oligonucleotide synthesis.

Numerous methods for the attachment of oligonucleotides and proteins on surfaces have been described. The reported covalent attachments of pre-made oligonucleotides onto glass surfaces have been always using modified oligonucleotides in order to increase reactivity and selectivity of oligonucleotides towards surfaces. Typical modifications involved the introduction of amino groups, or thio groups into 3'- and/or 5'-amino modified oligonucleotides onto epoxy surfaces. Stimpson et al. (*P.N.A.S.* 92:6379–6383 (1995)) discloses the generation of DNA chips for use in automated DNA diagnostic applications. To this effect, the Stimpson article discloses the immobilization of 3' amino-linked oligonucleotides into an organized array on a glycidoxypropyl silane treated glass slide.

Lamture et al. (*Nucleic Acids Res.* 22:2121–2125 (1994)) describes the immobilization of 3' amino modified oligonucleotides to a 3-glycidoxypropyl-trimethoxysilane coated silicon wafer in the presence of 0.1M KOH. The oligonucleotides are covalently immobilized to the solid support by means of a secondary amine linkage. Beattie et al. (*Clin. Chem.* 41:700–706 (1995)) discloses the immobilization of either 3' and/or 5' amino modified oligonucleotides to 3-glycidoxypropyltrimethoxysilane coated glass slides at a temperature of 60° C. Additionally, several other references generally related to the immobilization of oligonucleotides to a solid-support. Chrisey et al. (*Nucleic Acids Res.* 24:3031–3039 (1996), Guo et al. (*Nucleic Acids Res.* 22:45456–5465 (1994), Fahy et al. (*Nucleic Acids Res.* 21:1819–1826 (1993), Sliwkowski et al. (*Biochem. J.* 209:731–739 (1983) all disclose the immobilization of a 5' or 3' modified oligonucleotide to a solid-support.

The method of the present invention provides three distinct advantages over other covalent attachment chemistries for oligonucleotide array preparation. First, while the above-identified prior art references require that the oligonucleotide be either amino or thiol modified, the present invention discloses a method to covalently bond oligonucleotides with an "unmodified" 5' or 3'-OH to a solid surface. The present invention thus differs from conventional methods for the covalent attachment of oligonucleotides to solid phases in that it permits the covalent attachment of "unmodified" oligonucleotides. Accordingly, the present invention provides several significant improvements over the prior art. In particular, the present invention provides a low-cost, stable method for the covalent attachment of "unmodified" oligonucleotides to a silanized solid-phase wherein the covalently bound oligonucleotides have wide uses in genetic and combinatorial analysis involving nucleic acids or proteins. Covalent attachment of oligonucleotides onto solid phase surfaces is therefore achieved without modification of oligonucleotides, thereby dramatically reducing the cost and eliminating the variation in quality of modified oligonucleotides.

Second, the silanized surface of the present method provides a very hydrophobic surface which allows oligonucleotide probe droplets to form at specific and localized positions on the solid surface. Thus, for example, multiple probes can be patterned simultaneously on the surface using, for example, a robotic liquid delivery system or an ink-jet printing technique with no cross contamination between probes, even at a high probe density (10,000 probes/cm$^2$). Accordingly, the process can be easily automated and scaled-up using an off-the-shelf robot or ink-jet printing instrument. Standard covalent attachment chemistries require the use of photolithographic and laser patterning techniques which require multiple masking and lifting steps for high density DNA array preparation.

Third, unlike traditional techniques, the present method does not require the use of expensive crosslinking agents. These crosslinking agents are difficult to use because of their sensitivity to air and humidity. Therefore, the present method provides a new, efficient and inexpensive method for DNA array preparation, and particularly for large scale DNA array preparation.

In the preferred embodiment, this invention describes a method for immobilizing nucleic acids on silane coated solid phase surfaces which is useful in genetic analysis and other screening applications such as protein-DNA binding assays. The invention pertains to oligonucleotide arrays comprising silane coated solid phase surfaces and unmodified or modified oligonucleotides covalently attached to the silane coated solid phase, such arrays being useful for genetic analyses and combinatorial analyses involving nucleic acids or proteins. The features of the coated surface enable standardized patterning of unique oligonucleotides onto silane surface coatings.

In the most preferred embodiment, the invention provides for methods of covalent attachment of unmodified oligonucleotides onto mercapto-silanized surface or epoxy-silanized surfaces with high density and high stability. The ease of preparation of unmodified oligonucleotides coupled with stable ether (epoxy) or thio-ether (mercapto) linkage attachments renders this method the most cost effective, with little or no variation in terms of the quality of oligonucleotides, stability of attachment linkage and consistency in large scale batch to batch manufactures. Additionally, the hydrophobic property of silane surfaces also allows simultaneous patterning of multiple DNA probes in a high density and in a variety of array formats. Furthermore, a DNA array that is stable to high salt and denaturing conditions such as DMF, urea and elevated temperatures, has wide uses in miniaturized biotechniques such as genetic testing, sequencing by hybridization and combinatory selection of DNA binding molecules.

The covalent attachment of the present invention can be distinguished from other means of attachment, such as van der Waals interaction and ion—ion interactions. Thus, unlike other attachment means, the covalently immobilized oligonucleotide will not be released from the solid-phase during subsequent wash steps. The covalent attachment generally provides more stable binding than noncovalent attachment under elevated temperatures and upon other chemical treatment; thus, giving more flexibility for use in biochemical processes.

II. The Immobilization of Nucleic Acid Molecules Using Epoxy Chemistry

In a preferred embodiment of the present invention, a selective, highly efficient method is provided which employs an epoxy-based attachment chemistry to covalently attach nucleic acid molecules in an end selective manner to a solid-phase. Oligonucleotides have two free hydroxyl groups at the 5'- and 3'-ends which allow oligonucleotides to undergo chemical and/or enzymatic elongation, ligation and circularization. The differences in steric hindrances between these two end hydroxyl groups have enabled 5'-selective esterification, 5'-selective tritylation and 5'-selective oxidation in controlled conditions. Unmodified oligonucleotides for attachment to solid phases under certain controlled conditions thus have the potential for the 5'-OH to react preferentially over the 3'-OH towards epoxy activated surfaces. End-selective attachment is achieved in epoxy chemistry by taking advantage of differences in steric hindrance between the 5' and 3' end of the oligonucleotide. Accordingly, one could block either terminus (via phosphorylation, etc.) and therefore obtain a directionally oriented attachment between the solid phase and the unblocked terminus.

The covalent bond described in the epoxy-based preferred embodiment of the present invention is a covalent ether linkage. End selective attachment ensures that the full sequence of the immobilized oligonucleotide is accessible for any desired biochemical reaction. Since there is no need for any modification of oligonucleotides, this embodiment dramatically reduces the cost and variation in terms of the quality of oligonucleotides. The epoxy-based attachment chemistry allows attachment of all forms of DNA including pcr products or genomic DNA to the silanized surface. Furthermore, in the case of epoxy-based attachment chemistry, the chemical bonds between the silane layer and oligonucleotides are covalent ether linkages, which are stable to heat, high salt, and elevated temperatures.

III. The Immobilization of Nucleic Acid Molecules Using Mercapto Chemistry

The present invention describes in another preferred embodiment a random, highly efficient method which employs a mercapto-based attachment chemistry to covalently attach nucleic acid molecules in a non-specific manner to a solid-phase. The covalent bond described in this second preferred embodiment of the present invention is a covalent thioether linkage. Because this embodiment relies on non-specific binding, the full sequence of the immobilized oligonucleotide may not be accessible for all desired biochemical reactions. Since the mercapto group is very reactive in terms of radical reactions and easily deionized under lower pH (pH 9), this allows a variety of reactions to occur with nucleic acids. Heterocyclic purines (electron rich system stabilizing radicals, particularly at position 7 of purines) and pyrimidines (electron deficient, a nucleophile acceptor) in oligonucleotides are good acceptors for either nucleophilic attack or radical reactions. In mercapto chemistry the highly reactive mercapto groups allow mild conditions for attachment. The resulting array can undergo a variety of biochemical reactions and allows hybridization with high efficiency. The mercapto-based attachment chemistry allows attachment of all forms of DNA including pcr products or genomic DNA to the silanized surface. Furthermore, in the case of mercapto-based attachment chemistry, the chemical bonds between the silane layer and oligonucleotides are covalent thioether linkages, which are stable to heat, high salt, and elevated temperatures.

The unmodified nucleic acid molecules, described in the present invention, may be either genomic DNA (i.e., DNA containing a non-translated region), cDNA (i.e., DNA lacking non-translated regions) or RNA; the nucleic acid molecule may also be either single or double stranded. While any unmodified nucleic acid molecule may be immobilized using the present invention, the preferred nucleic acid molecule of the present invention is an unmodified single-stranded synthetic oligonucleotide. The method for making a synthetic oligonucleotide has been previously described by Gait, M. J. (*Oligonucleotide Synthesis, A Practical Approach*, IRL Press Ltd., Oxford (1984)) and Sinha, N. D. et al. (*Nucl. Acids Res.* 12:4539–4557 (1984)) (herein incorporated by reference).

Synthesis of unmodified oligonucleotides of about 10 to about 250 nucleotides in length may be performed on an ABI 392 DNA/RNA synthesizer according to phosphoramidite chemistry.

After synthesis, the unmodified oligonucleotides can be purified (for example, using an HPLC column) to separate the full-length oligonucleotides from any contaminating prematurely terminated (i.e., shortened) oligonucleotides. Prior to use in the coupling reaction, the oligonucleotides are concentrated, and, if desired, the molar concentration of the oligonucleotides can be determined.

Although any of a variety of glass or plastic solid supports can be used in accordance with the methods of the present invention, glass is the preferred support. The support can be fashioned as a bead, dipstick, test tube, pin column, etc. However, an especially preferred support is a glass slide. Alternatively, the solid support can be a form of polystyrene plastic (e.g., 96-well microtiter plate, etc.).

Many different mercaptosilane compounds such as 3-mercaptopropyltrimethoxy-silane, 3-mercaptopropyltriethoxysilane, (mercapto-methyl) dimethoxysilane and (mercaptoethyl)ethyldimethoxysilane, etc. can be used in the present invention for coating the solid support with sulfhydryl groups. The general formula for a mercaptosilane that can be used in this invention is:

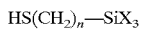

wherein X is a hydrolyzable group such as alkoxy, acyloxy, amine or halide, etc. All of the mercaptosilanes mentioned above are commercially available from United Chemical, Inc. or Aldrich Chemical Company, Inc.

The silane can be coated onto the solid-phase by any of a number of means. For example, the mercaptosilane can be deposited onto the solid surface as an aerosol or a vapor. Alternatively, the silane can be spread onto the solid-surface by mechanical means (e.g., a spreader bar, a saturated cloth, etc.).

An important feature of the present invention is the hydrophobic nature of silanes. Because of this feature, it is possible for an aqueous solution to form extremely well defined beads on the surface of any solid support coated with mercaptosilane. With an automated delivery system, such as a Hamilton robot or ink-jet printing method, it is possible to form a very complex array of oligonucleotide probes on a mercaptosilane coated glass slide. Such methods can deliver nano to pico-liter size droplets with sub-millimeter spacing. Because the aqueous beads are extremely well defined, it is possible to create an array with an extremely high density of oligonucleotide probes. Thus, it is possible to create arrays having greater than about 10,000 probe droplets/cm².

IV. The Use of Immobilized Nucleic Acid Molecules

Immobilized nucleic acid molecules, and more preferably, immobilized oligonucleotides, make an ideal diagnostic tool. Specifically, their versatility and simplicity make them ideal diagnostic tools for the detection of infectious and genetic diseases, mutation analysis, etc.

Although the manner in which the nucleic acid molecules are immobilized to the solid support can be random, one of the preferred embodiments of the invention is to arrange the nucleic acid molecules into an ordered array. As used herein, an array is an orderly arrangement of nucleic acid molecules, as in a matrix of rows and columns. The chemistry of the present invention is such that an individual array can contain either a finite or an infinite number of unique immobilized nucleic acid molecules.

There are two preferred methods to make a nucleic acid array: one is to synthesize the specific oligonucleotide sequences directly onto the solid-phase in the desired pattern (Southern, et al., *Nucl. Acids Res.* 22:1368–1373 (1994); Maskos, et al., *Nucl. Acids Res.* 20:1679–1684 (1992); and Pease, et al., *Proc. Natl. Aced. Sci.* 91:5022–5026 (1994); all of which are herein incorporated by reference) and the other is to pre-synthesize the oligonucleotides on an automated DNA synthesizer (such as an ABI 392 and then attach the oligonucleotides onto the solid-phase at specific locations (Lamture, et al., *Nucl. Acids Res.* 22:2121–2125 (1994) and (Smith, et al., *Nucl. Acids Res.* 22:5456–5465 (1994) both herein are incorporated by reference). In the first method, the efficiency of the coupling step of each base will affect the quality and integrity of the nucleic acid molecule array. This method generally yields a large percentage of undesired incomplete (shortened) sequences which can create problems in the analysis step and effect the integrity of the analysis. Thus, the quality and integrity of an array synthesized according to the first method is inversely proportional to the length of the nucleic acid molecule. Specifically, the synthesis of longer oligonucleotides results in a higher percentage of incomplete, shortened sequences.

A second, more preferred, method for nucleic acid array synthesis utilizes an automated DNA synthesizer for DNA synthesis. The controlled chemistry of an automated DNA synthesizer allows for the synthesis of longer, higher quality DNA molecules than is possible with the first method. Also, the nucleic acid molecules synthesized according to the second method can be purified prior to the coupling step. Therefore, the quality of the nucleic acid molecule array can be expected to be much higher than the quality of the nucleic acid array of the first method. However, a simple, effective and specific oligonucleotide coupling chemistry is lacking for the attachment of presynthesized oligonucleotides. The present invention describes a simple, effective and efficient method for coupling a pre-synthesized unmodified oligonucleotide onto a solid-phase by means of either an ether or thioether covalent linkage.

A. Hybridization Detection of PCR Products

Thus, for example, covalently immobilized nucleic acid molecules may be used to detect specific PCR products by hybridization where the capture probe is immobilized on the solid phase (Ranki et al., Gene 21: 77–85 (1983); Keller et al., J. Clin. Microbiol. 29: 638–641 (1991); Urdea et al., Gene 61: 253–264 (1987). A preferred method would be to prepare a single-stranded PCR product before hybridization. A sample, suspected to contain the target molecule, or an amplification product thereof, would then be exposed to the solid-surface and permitted to hybridize to the bound oligonucleotide.

The methods of the present invention do not require that the target nucleic acid contain only one of its natural two strands. Thus, the methods of the present invention may be practiced on either double-stranded DNA, or on single-stranded DNA obtained by, for example, alkali treatment of native DNA. The presence of the unused (non-template) strand does not affect the reaction.

Where desired, however, any of a variety of methods can be used to eliminate one of the two natural stands of the target DNA molecule from the reaction. Single-stranded DNA molecules may be produced using the single-stranded DNA bacteriophage M13 (Messing, J. et al., *Meth. Enzymol.* 101:20 (1983); see also, Sambrook, J., et al. (In: *Molecular Cloning: A Laboratory Manual,* Cold Spring Harbor Laboratory Press, Cold Spring Harbor, N.Y. (1989)).

Several alternative methods can be used to generate single-stranded DNA molecules. Gyllensten, U. et al., (*Proc. Natl. Acad. Sci. (U.S.A.)* 85:7652–7656 (1988) and Mihovilovic, M. et al., (*BioTechniques* 7:14 (1989)) describe a method, termed "asymmetric PCR," in which the standard "PCR" method is conducted using primers that are present in different molar concentrations. Higuchi, R. G. et al. (*Nucleic Acids Res.* 17:5865 (1985)) exemplifies an additional method for generating single-stranded amplification products. The method entails phosphorylating the 5'-terminus of one strand of a double-stranded amplification product, and then permitting a 5'→3' exonuclease (such as T7 gene exonuclease) to preferentially degrade the phosphorylated strand.

Other methods have also exploited the nuclease resistant properties of phosphorothioate derivatives in order to generate single-stranded DNA molecules (Benkovic et al., U.S. Pat. No. 4,521,509; Jun. 4, 1985); Sayers, J. R. et al. (*Nucl. Acids Res.* 16:791–802 (1988); Eckstein, F. et al., *Biochemistry* 15:1685–1691 (1976); Ott, J. et al., *Biochemistry* 26:8237–8241 (1987)).

Most preferably, such single-stranded molecules will be produced using the methods described by Nikiforov, T. (commonly assigned U.S. Pat. No. 5,518,900, herein incorporated by reference). In brief, these methods employ nuclease resistant nucleotide derivatives, and incorporate such derivatives, by chemical synthesis or enzymatic means, into primer molecules, or their extension products, in place of naturally occurring nucleotides.

Suitable nucleotide derivatives include derivatives in which one or two of the non-bridging oxygen molecules of the phosphate moiety of a nucleotide has been replaced with a sulfur-containing group (especially a phosphorothioate), an alkyl group (especially a methyl or ethyl alkyl group), a nitrogen-containing group (especially an amine), and/or a selenium-containing group, etc. Phosphorothioate deoxyribonucleotide or ribonucleotide derivatives are the most preferred nucleotide derivatives. Methods of producing and using such phosphorothioate derivatives are disclosed by Nikiforov, T. (U.S. Pat. No. 5,518,900).

B. Solid Phase DNA Sequencing

The methods of the present invention may also be used in the practice of solid-phase sequencing as described by Khrapko, K. R. et al. (DNA Seq., 1: 375–388 (1991) and Drmanac, R. and Crkvenjakov, R., *Int. J. Genome Res.*, 1: 1–11 (1992)), both herein are incorporated by reference.

C. GBA™ Genetic Bit Analysis

The methods of the present invention may also be used to immobilize the oligonucleotides that are used in the GBA™ Genetic Bit Analysis (Goelet, P. et al., PCT Application No. 92/15712), herein incorporated by reference. GBA™ Genetic Bit Analysis a solid-phase method for the typing of single-nucleotide polymorphisms. Oligonucleotides having a defined sequence complementary to a region that lies immediately proximal or distal to the variable nucleotide of a polymorphism would thus be provided to a polystyrene microtiter well or glass plate, and incubated with a salt, in accordance with the above-described methods.

The immobilized primer is then incubated in the presence of a DNA molecule (preferably a genomic DNA molecule) having a single nucleotide polymorphism whose immediately 3'-distal sequence is complementary to that of the immobilized primer. Preferably, such incubation occurs in the complete absence of any dNTP (i.e. dATP, dCTP, dGTP, or dTTP), but only in the presence of one or more chain terminating nucleotide derivatives (such as a dideoxynucleotide derivative), and under conditions sufficient to permit the incorporation of such a derivative onto the 3'-terminus of the primer. As will be appreciated, where the polymorphic site is such that only two or three alleles exist (such that only two or three species of ddNTPs, respectively, could be incorporated into the primer extension product), the presence of unusable nucleotide triphosphate(s) in the reaction is immaterial. In consequence of the incubation, and the use of only chain terminating nucleotide derivatives, a single dideoxynucleotide is added to the 3'-terminus of the primer. The identity of that added nucleotide is determined by, and is complementary to, the nucleotide of the polymorphic site of the polymorphism.

Using the method described in the present patent application, oligonucleotide primers can be immobilized on solid phases like polystyrene or glass, hybridized to PCR-derived, single-stranded templates, and subjected to enzymatic extension at their 3'-ends by a single, labeled ddNTP. The nature of the incorporated ddNTP is determined by the nucleotide that is located in the opposite strand (the polymorphic nucleotide). This assay can be conveniently carried out both in polystyrene ELISA plates, or on glass slides.

In this embodiment, the nucleotide of the polymorphic site is thus determined by assaying which of the set of labeled nucleotides has been incorporated onto the 3'-terminus of the bound oligonucleotide by a primer-dependent polymerase. Most preferably, where multiple dideoxynucleotide derivatives are simultaneously employed, different labels will be used to permit the differential determination of the identity of the incorporated dideoxynucleotide derivative.

D. Ligase-Mediated GBA™

The methods and reagents of the present invention can also be used in concert with a polymerase/ligase mediated polymorphic interrogation assay. This assay, termed ligase-mediated GBA™ genetic bit analysis, is a more specific version of the GBA™ genetic bit analysis assay. The additional specificity arises from the addition of a second hybridization step and a ligation step.

In this assay, two oligonucleotides are employed. The first oligonucleotide is a primer that is complementary to the immediately 3'-distal invariant sequence of the polymorphism. The 3'-end of the oligonucleotide is attached to the plate. A second linker oligonucleotide is complementary to the 5'-proximal sequence of the polymorphism being analyzed, but is incapable of hybridizing to the first oligonucleotide. The second linker oligonucleotide is phosphorylated at both its 3' and 5' ends.

These oligonucleotides are incubated in the presence of DNA containing the single nucleotide polymorphism that is to be analyzed, and at least one 2'-deoxynucleotide 5'-triphosphate. The incubation reaction further includes a DNA polymerase and a DNA ligase. The tethered and soluble oligonucleotides are thus capable of hybridizing to the same strand of the target molecule under analysis. The sequence considerations cause the two oligonucleotides to hybridize to the proximal and distal sequences of the single nucleotide polymorphism (SNP) that flank the variable nucleotide of the polymorphism, and to be separated by a single nucleotide at the precise position of the variability.

The presence of a polymerase and the 2'-deoxynucleotide 5'-triphosphate complementary to the nucleotide present in the variable site of the polymorphism permits the extended primer to be ligated to the bound oligonucleotide, thereby immobilizing the primer. The identity of the polymorphic site that was opposite the single nucleotide can then be determined by any of several means. In a preferred embodiment, the 2'-deoxynucleotide 5'-triphosphate of the reaction is labeled, and its detection thus reveals the identity of the complementary nucleotide of the polymorphic site. Several different 2'-deoxynucleotide 5'-triphosphates may be present, each differentially labeled. Alternatively, separate reactions can be conducted, each with a different 2'-deoxynucleotide 5'-triphosphate. In an alternative sub-embodiment, the 2'-deoxynucleotide 5'-triphosphates are unlabeled, and the soluble oligonucleotide is labeled. In this embodiment, the primer that is extended is immobilized on the polystyrene. Separate reactions are conducted, each using a different unlabeled 2'-deoxynucleotide 5'-triphosphate.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth and as follows in the scope of the appended claims.

Having now generally described the invention, the same will be more readily understood through reference to the following examples which are provided by way of illustration, and are not intended to be limiting of the present invention unless specified. All patents, patent applications and publications mentioned herein are incorporated by reference in their entirety.

EXAMPLE 1

EPOXY-BASED CHEMISTRY

Attachment was obtained by a two-step process of silane treatment and oligonucleotide binding. Glass slides were etched in 25% aqueous ammonium hydroxide, rinsed in milliQ water, then in 95% ethanol. They were treated for about 30 minutes in glycidoxy propyl trimethoxysilane (95% ethanol, pH 4.5). Slides were cured at 65° C. for at least 12 hours. 2.5–10 uM conc. of oligonucleotides in an alkaline solution (12.5 mm NaOH or KOH) were applied onto cured slides in any desired array formats, in a covered chamber overnight, after which they were stored in water or a covered chamber for later use. A functional test with hybridization and enzymatic reactions gave the desired signal with 400>1 signal to noise ratio by ELF indirect detection reading and radioisotope quantitation (FIG. 1). FIG. 1 shows the results of GBA functional assay of epoxy-based attachment chemistry. The 25-mer primer with (T)10 spacer arm at 5' was used for attachment. Standard GBA conditions were used in terms of nucleoside triphosphate concentration and enzyme concentration and reaction conditions. Synthetic template 1 was designed to give an "A" signal and synthetic template 2 was designed to give a "T" signal. Single base extension (GBA signal) was obtained only with appropriate template, by using ELF indirect detection and also by CCD camera imaging. The signal to noise ratio (S/N) was greater than 400:1.

Additionally, an attachment experiment was designed with the following end-blocked oligonucleotides 5'-end blocked, 3'-end blocked, or both end blocked. The end blocks were achieved by phosphorylation of the end hydroxyl groups during automated DNA synthesis. The attachment for each type of oligonucleotides was quantified by phosphor image analysis and then the ratio of end selectivity was determined. The 5'-end selective attachment of unmodified oligonucleotides to epoxy silanized surfaces was demonstrated with a selectivity ratio of at least 5:1. Attachment through heterocyclic aminos was minimal in certain conditions tested (Table 1).

TABLE 1

| Oligo conc. used for att. (uM) | 10 | 5 | 2.5 | 1.25 |
|---|---|---|---|---|
| 5'-att. (incl. middle) pmole/7 mm$^2$ | 1.0 | 1.6 | 1.4 | 0.9 |
| 3'-att. (incl. middle) pmoles/7 mm$^2$ | 0.143 | 0.29 | 0.42 | 0.48 |
| middle att. pmole/7 mm$^2$ | 0.13 | 0.09 | 0.35 | 0.235 |
| 5'-att./3'-att. (after sub middle) | 87 | 7.55 | 15 | 21 |

TABLE 1-continued

| | | | | |
|---|---|---|---|---|
| 5'-att./middle att. | 6.7 | 16 | 3 | 2.8 |
| 3'att./middle att. | 0.077 | 2.2 | 0.2 | 1.04 |
| 3'- & 5-att./middle att. | 6.8 | 19 | 3.2 | 3.8 |

Table 1 shows the end selective attachment of un-modified oligonucleotides by epoxy-based chemistry. Attachment was performed on an epoxy silanized slide with various concentrations of oligonucleotides in 12.5 mM NaOH for overnight and washed sequentially with TNTw and 50 mM NaOH. 5'-att refers to the attachment reading of 3'-phosphorylated oligonucleotides; 3'-att refers to the attachment reading of 5'-phosphorylated oligonucleotides. Middle att refers to the heterocyclic amino attachment reading of both 3'- and 5'-end blocked oligonucleotides. The $^{32}$P isotopes images were analyzed on phosphor image quanta software. Attachment at a concentration of 10 uM gave the best selectivity ratio of 87:1 of 5'-end vs. 3'-end attachment. Attachment at concentration of 5 uM gave the best end selectivity ratio of 19:1 of 3'-plus 5'-vs. middle attachment. These results were based on one slide only, however, a number of slides expressed a trend of optimum concentration at 2.5–5 uM for 5'-end selective attachment. In addition, epoxy-silanized surfaces are air-, moisture-, and heat-stable and showed no nonspecific binding to proteins and oligonucleotides under conditions tested. In summary, 5'-end selective attachment of oligonucleotides was demonstrated without modification of oligonucleotides.

EXAMPLE 2

MERCAPTO-BASED CHEMISTRY

Figure 2:
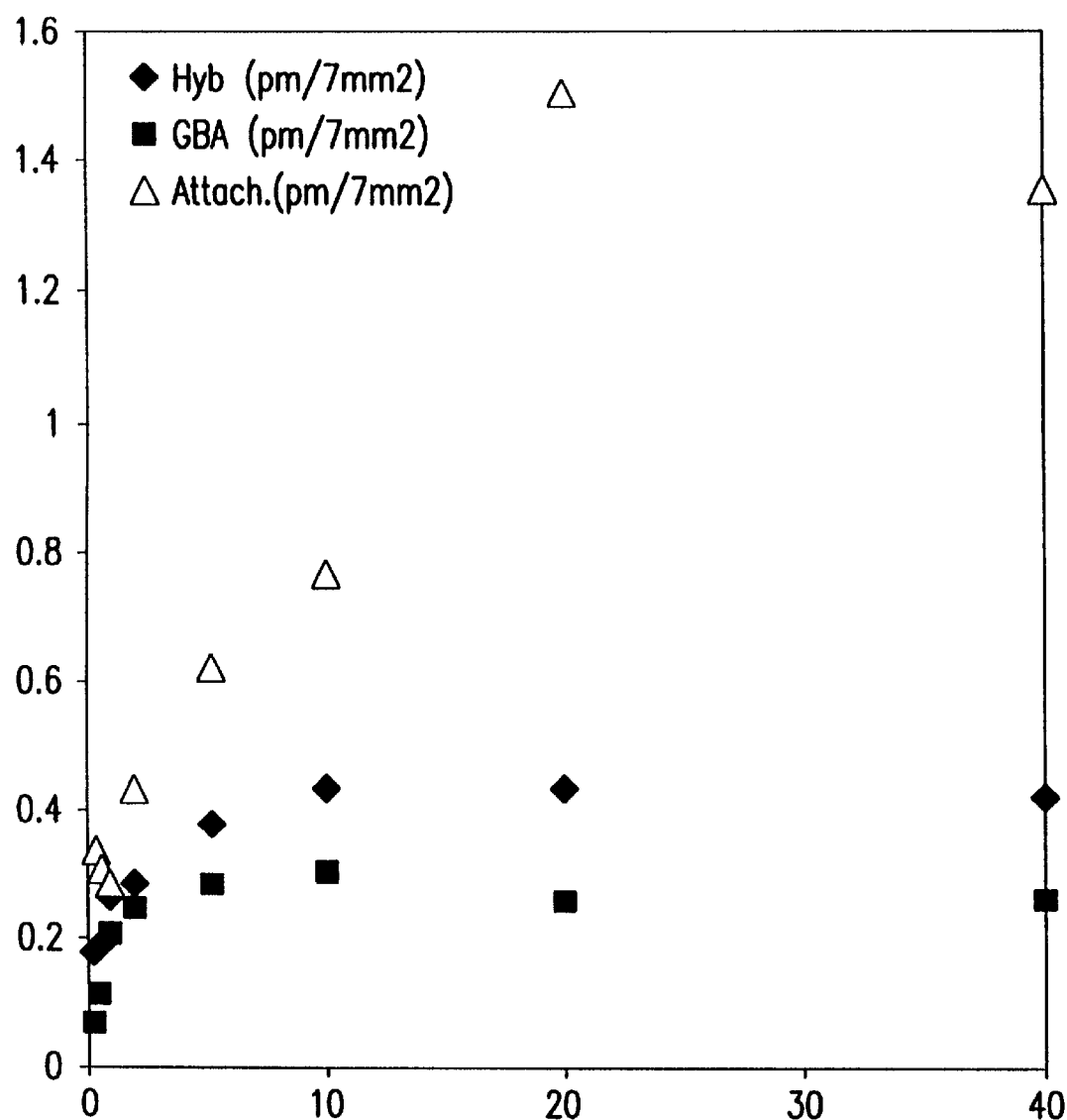
FIG. 2 shows the results of mercapto-based attachment chemistry and functional assay by hybridization and GBA.

Attachment was obtained by a two-step process of silane treatment and oligonucleotide binding. Glass slides were etched in 25% aqueous ammonium hydroxide, rinsed in milliQ water, then in 95% ethanol. They were treated for about 30 minutes in 3-mercapto-propyl-trimethoxysilane (MPTS). Slides were cured for at least 24 hours under dry inert gas (Ar or $N_2$). 2.5–10 uM conc. of oligonucleotides in an alkaline solution were applied onto cured slides in any desired array formats, in a covered chamber for an overnight, after which they were stored in water or a covered chamber for later use. A functional test with hybridization and enzymatic reactions gave the desired signal (FIG. 2). FIG. 2 shows the results of mercapto-based attachment chemistry and functional assay by hybridization and GBA. The data was based on phosphor imaging quanta analysis. The X axis represents the input concentration of oligonucleotides used for attachment from 0.3125 uM to 40 uM. Oligo attached is represented by the triangle (pmole/7 mm$^2$), the diamond represents hybridization and the square represents GBA signals (ddATP extension). $^{32}$P labeled oligonucleotides were used for determining the attachment density. The $^{32}$P 5'-template was used for assessing the hybridization efficiency. The GBA efficiency was determined by incorporation of $^{32}$P-ddATP with exo-klenow DNA polymerase without the presence of other cold dideoxynucleotides. The GBA efficiency and hybridization reached saturation at the attachment input of 10 uM.

Additionally, experiments were performed for attachment of dye-labeled nucleotides to mercapto propyl silanized slides which showed stronger signals for A and G and weaker signals for C and T, which favors the hypothesis that radical mechanisms are more involved than nucleophilic attacks. The attachment of $^{32}$P labeled oligonucleotides and fluorescein labeled oligonucleotides was demonstrated and quantified (FIG. 2). The attachment results achieved in terms of attachment density, hybridization and genetic bit analysis efficiency were compatible with epoxy chemistry and chemistries reported by others.

EXAMPLE 3

THE RELATIONSHIP BETWEEN PRIMER DENSITY AND HYBRIDIZATION EFFICIENCY

Hybridization efficiency is positively related to the surface density of the attached primer. In this study, increasing amounts of the BRAC1 primer 5' $(T)_{10}$ TCA TTA ATG CTA TGC AGA AAA TCT TAG (SEQ ID No. 1) are covalently attached to a solid surface according to the methods described above. Table 2 shows the results for epoxy-based attachment vs. hybridization efficiency. The data was based on phosphor imaging quanta analysis. 3'-phosphorylated oligonucleotides were used for attachment and 5'-phosphorylated templates were used for hybridization. A low surface coverage would presumably yield a corresponding low hybridization signal. Conversely, high surface densities might result in steric interference between the covalently immobilized oligonucleotides thereby impeding access to target DNA. The results indicated that with higher coverage up to 1.78 pmoles/7 mm$^2$, a higher hybridization efficiency was obtained. Increased primer density is associated with increased hybridization efficiency. Accordingly, hybridization efficiency is affected by the stability of the primer attachment.

TABLE 2

| conc. for att. | covalent att | Hybridization |
|---|---|---|
| 40 uM | 0.19 | 0.1 + 0.015 |
| 20 | 0.42 | 0.14 + 0.00 |
| 5 | 1.78 | 0.58 + 0.005 |
| 2.5 | 1.61 | 0.43 + 0.03 |
| 1.25 | 0.98 | 0.29 + 0.05 |
| 0.625 | 0.42 | 0.17 + 0.01 |

EXAMPLE 4

GENETIC BIT ANALYSIS COMPATIBILITY

A GBA primer having a poly-$T_{10}$ residue long spacer arm is attached to the glass surface by means of the previously described epoxy-based chemistry or mercapto-based chemistry. Standard GBA biochemistry is used to analyze two synthetic templates. Each synthetic template is hybridized to GBA primer immobilized to the treated glass slide and treated with an extension mix containing all of the extension reaction components, exonuclease-free Klenow fragment of the E. coli polymerase and each of four fluorescein-labeled ddNTP's and co-ddNTP's or $^{32}$P-ddATP. The signal was recorded by enzyme-mediated fluorescence using a Cytoflour II fluorescent plate reader (FIG. 1) or phosphor image quanta analysis. FIG. 1 shows the results of GBA functional assay of epoxy-based attachment chemistry. The 27-mer primer with (T)10 spacer arm at 5' was used for attachment (SEQ ID No. 1). Standard GBA conditions were used in terms of nucleoside triphosphate concentration and enzyme concentration and reaction conditions. Synthetic template 1 5' ACA CTC TAA GAT TTT CTG CAT AGC ATT AAT (SEQ ID No. 2) was designed to give an "A" signal and synthetic template 2 5' GGA CAC TAA GAT TTT CGT CAT AGC ATT AAT (SEQ ID No. 3) was designed to give a "T"

signal. Single base extension (GBA signal) was obtained only with the appropriate template, by using ELF indirect detection and also by CCD camera imaging. The signal to noise ratio (S/N) was greater than 400:1.

DNA Samples. Genomic DNA was isolated using the SDS/Proteinase K procedure (Maniatis, T. Molecular Cloning, A Laboratory Manual, Cold Spring Harbor Laboratory Press, Cold Spring Harbor (1989)) from peripheral blood nucleated cells of humans or horses enriched from red blood cells by selective lysis accomplished by diluting blood with a three fold volume excess of ACK lysing buffer (0.15 M ammonium chloride, 1 mM potassium bicarbonate, 0.1 mM EDTA). Oligonucleotides were prepared by solid-phase phosphoramidite chemistry using an Applied Biosystems, Inc. Model 391 automated DNA synthesizer (Foster City, Calif.). In the case of primers used in Genetic Bit Analysis (GBA) reactions, detritylation was not performed following the final cycle of synthesis and the full-length oligonucleotide was purified using the Applied Biosystems oligonucleotide purification cartridge (OPC) as recommended by the manufacturer. For most PCR reactions, primers were used directly by drying down the de-protection reaction.

Table 3 depicts the results of an experiment employing a synthetic template 1 5' ACA CTC TAA GAT TTT CTG CAT AGC ATT ATT (SEQ ID No. 2)(designed to give a GBA signal in base A) and a synthetic template 2, 5' GGA CAC TAA GAT TTT CGT CAT AGC ATT AAT (SEQ ID No. 3)(designed to give a signal in base T). The primer used was $(T)_{10}$ TCA TTA ATG CTA TGC AGA AAA TCT TAG (SEQ ID No. 1). Both signals give strong signals in the expected bases with virtually no noise observed in the other bases (the Signal to Noise Ratio ranged from 520:1 to 600:1).

TABLE 3

| | Fluorescent Counts | |
|---|---|---|
| Nucleotide Inserted | Template 1 | Template 2 |
| A | ≈600 | 1 |
| C | ND | ND |
| G | ND | ND |
| T | 1 | ≈520 |

EXAMPLE 5

PREPARATION OF AN OLIGONUCLEOTIDE ARRAY BY INK-JET PRINTING

Another method for the automated delivery of the oligonucleotide solution employs an ink-jet printing technique performed by MicroFab (MicroFab Technologies, Inc., Plano, Tex.). In one experiment, four different spot spacings (center to center) and eight different droplet sizes are tested on the mercaptosilane coated surface using an oligonucle otide labeled at the 3'-terminus with fluorescein. The format of the slides, depicted in Table 4, are as follows:

TABLE 4

| Slide No. | Spot Spacing | Row (Row Spacing = 6 mm) | | |
|---|---|---|---|---|
| | | Row 1 | Row 2 | Row 3 |
| Slide 1 | 1 mm | 5 nl | 10 nl | 25 nl |
| Slide 2 | 0.5 mm | 1 nl | 2 nl | 5 nl |
| Slide 3 | 250 μm | 250 pl | 500 pl | 1 nl |
| Slide 4 | 125 μm | 125 pl | 250 pl | N/A |

The labeled oligonucleotides are detected using a Molecular Dynamic FluorImager 595. The ink-jet printing technique is a suitable method for the manufacture of oligonucleotide arrays with sub-millimeter spacing and nano to pico-liter droplet sizes. As such, the ink-jet printing technique is suitable for large scale manufacture of oligo arrays.

EXAMPLE 6

PREPARATION OF AND OLIGONUCLEOTIDE ARRAY WITH AN AUTOMATIC PIPETING ROBOT

A Hamilton 2200 automated pipeting robot is used to make arrays of oligonucleotide drops, ranging in size from about 100 nl to about 250 nl, with 1 mm spacing between dots. The small volumes of oligonucleotide solution used with the automated pipeting robot allows for rapid drying of the oligonucleotide drops. As in the ink-jet printing method, a Hamilton robot can be programmed to deliver nano to pico-liter size droplets with sub-millimeter spacing.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth and as follows in the scope of the appended claims.

What is claimed is:

1. A composition comprising a nucleic acid molecule covalently coupled to a solid support by a silane selected from the group consisting of 3-mercapto-propyl-trimethoxysilane and mercapto-alkyl-trimethoxysilane.

2. The composition of claim 1, wherein the solid support is selected from the group consisting of glass and plastic.

3. The composition of claim 2, wherein said glass is a microscope slide.

4. The composition of claim 2, wherein said plastic is polystyrene plastic.

5. The composition of claim 1, wherein said solid support is selected from the group consisting of a bead, a plate, a column, a pin and a dipstick.

6. The composition of claim 1, wherein more than one nucleic acid molecule is covalently coupled to said solid support.

7. The composition of claim 6, wherein said nucleic acid molecules are covalently coupled to said solid support in an array.

8. A composition comprising an array of nucleic acid molecules each nucleic acid molecule covalently coupled to a solid support by a silane selected from the group consisting of 3-mercapto-propyl-trimethoxysilane and mercapto-alkyl-trimethoxysilane.

9. The composition of claim 8, wherein the solid support is selected from the group consisting of glass and plastic.

10. The composition of claim 8, wherein the solid support is a 96-well microtiter plate.

11. The composition of claim 9, wherein said glass is a microscope slide.

12. The composition of claim 9, wherein said plastic is polystyrene.

13. The composition of claim 8, wherein said solid support is selected from the group consisting of a bead, a plate, a column, a pin and a dipstick.

14. A composition comprising a nucleic acid molecule covalently coupled to a solid support wherein said nucleic acid molecule is covalently coupled to said support by a silane thioether linkage.

15. A composition comprising an array of nucleic acid molecules coupled to a solid support wherein said nucleic acid molecules are covalently coupled to said support by silane thioether linkages.

16. A nucleic acid molecule covalently attached to a solid support by a mercapto silane.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (xi) SEQUENCE DESCRIPTION: SEQ ID NO:1:

TTTTTTTTTT TCATTAATGC TATGCAGAAA ATCTTAG                37

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:2:

ACACTCTAAG ATTTTCTGCA TAGCATTATT                        30

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

GGACACTAAG ATTTTCGTCA TAGCATTAAT                        30